United States Patent
Dobkin

[11] Patent Number: 5,902,275
[45] Date of Patent: May 11, 1999

[54] SURGICAL ATTACHMENT DEVICE FOR USE WITH ANGIOPLASTY DEVICES AND THE LIKE

[76] Inventor: William R. Dobkin, 6020 Lido La., Long Beach, Calif. 90803

[21] Appl. No.: 08/840,512

[22] Filed: Apr. 21, 1997

[51] Int. Cl.⁶ .................................................. A61M 5/32
[52] U.S. Cl. .................................. 604/174; 128/DIG. 26
[58] Field of Search .................................. 604/174, 179, 604/177, 180, 283; 128/DIG. 26; 24/3.9, 3.11, 268, 437, 438; 248/51, 74.2, 205.3, 316.8

[56] References Cited

U.S. PATENT DOCUMENTS

| | | | |
|---|---|---|---|
| 3,286,963 | 11/1966 | Bergman . | |
| 3,696,920 | 10/1972 | Lahay | 206/63.2 |
| 4,753,615 | 6/1988 | Uddo, Jr. et al. | 128/DIG. 26 |
| 5,024,404 | 6/1991 | Ballard | 248/62 |
| 5,084,026 | 1/1992 | Shapiro | 604/174 |
| 5,112,312 | 5/1992 | Luther | 604/177 |
| 5,643,217 | 7/1997 | Dobkin | 604/174 |
| 5,681,290 | 10/1997 | Alexander | 604/174 |
| 5,702,371 | 12/1997 | Bierman | 604/174 |
| 5,735,821 | 4/1998 | Dobkin | 604/174 |

FOREIGN PATENT DOCUMENTS

| | | | |
|---|---|---|---|
| 831757 | 7/1952 | Germany | 128/DIG. 26 |
| WO 88/04185 | 6/1988 | WIPO . | |

Primary Examiner—Wynn Wood Coggins
Assistant Examiner—Sharon Finkel
Attorney, Agent, or Firm—Kenneth W. Float

[57] ABSTRACT

Apparatus for securing a relatively small diameter wire or tube, and in particular, a small diameter guide wire and an angioplasty catheter that are inserted into a patient during an angioplasty or similar operation. The apparatus has a flexible member comprising a base portion, first and second abutting flexible portions attached to the base portion, and an opening having a diameter suitable for loosely securing the wire and catheter formed at an interface between the abutting flexible portions. An adhesive layer, typically having a backing layer, is disposed on the bottom of the flexible member. A preferred embodiment of the apparatus may be formed such that the first and second flexible portions extend outward in lateral directions away from the top of the opening. First and second base portions are connected to an external wall of the opening by flanges. The respective flexible portions and base portions have transverse ribs to provide added strength. The adhesive and backing layers are disposed on the bottom of both base portions.

12 Claims, 2 Drawing Sheets

SURGICAL ATTACHMENT DEVICE FOR USE WITH ANGIOPLASTY DEVICES AND THE LIKE

BACKGROUND

The present invention relates generally to medical equipment, and more particularly, to a surgical attachment device that is used to secure a small diameter guide wire that is used to insert an angioplasty device into a patient during an angioplasty operation, along with various catheters used during the operation.

During surgical operations, it is customary for surgeons and other operating room personnel to employ suction tubes to remove blood, tissue and other cellular debris from a patient that is undergoing an operation, and air-driven pneumatic tools that are driven by an air source(s) coupled to the tools by way of pneumatic hoses. Furthermore, it is customary to use electrosurgical instruments that are used as cutting and coagulation tools during surgery. These electrosurgical instruments are connected to electrical equipment by way of electrical cables. Unipolar electrosurgical instruments transmit current through the patient to a grounding pad, while bipolar electrosurgical instruments transmit current between the two heads of bipolar forceps. The electrosurgical instruments, pneumatic tools, and cables are used in almost all surgeries. More recently, endoscopic surgery has proliferated. These surgeries require fiber optic light cables and video camera cables passing to and from the operative field, respectively.

During surgery, it is common practice to store the electrosurgical instruments and tools in a self-adherent plastic pocket of a drape that is disposed over the patient when they are not in use. This also provides easy access for the surgeon. The cables and hoses that connect the electrosurgical instruments and tools to their electrical equipment, air sources and endoscopic equipment are loosely gathered together adjacent an extremity of the patient and are secured by wrapping a portion of the drape around the cables and then holding them in place using a surgical clamp. In a similar fashion, the suction tubes are also routed and clamped in place, typically by the same type of surgical clamp. As should be clear from this typical operating room scenario, the cables are not very well controlled and in many instances interfere with the operation, or may become dislodged or contaminated.

To improve these operating room conditions, the present inventor has developed a number of surgical attachment devices that may be used to secure the tubes, cables and hoses during operations. Such surgical attachment devices are disclosed in U.S. Pat. No. 5,643,217, filed Jan. 17, 1995 and U.S. Pat. No. 5,735,821, filed Oct. 23, 1995. The present invention provides for an improvement to these devices that specifically address securing small diameter wires, such as guide wires and catheters used during angioplasty operations, along with angiography, angioplasty, coronary artery stent and laser catheters, and the like.

With specific regard to the present invention, during an angioplasty operation, typically, an angiogram guide wire and catheter are inserted into the femoral artery of a patient and maneuvered until they are located at a desired position. Angiograms are performed to determine the state of the blocked artery. After the angiograms are performed, the angiogram catheter and angiogram guide wire are replaced. The angiograms are analyzed prior to the operation and during following procedures.

Then, the angioplasty operation is undertaken. A relatively long length of small diameter angioplasty guide wire is then inserted into the femoral artery and is maneuvered until it arrives at the blocked artery location, typically using the angiogram catheter as a guide. The angioplasty wire is on the order of 0.014 inches in diameter. The angiogram catheter is then removed by sliding it over the angioplasty guide wire. An angioplasty catheter (or other device, such as angioplasty stent or laser catheters, for example) is then slid over the angioplasty guide wire while holding the exposed end of the angioplasty guide wire and is maneuvered until it is in position to expand the artery adjacent to the blockage. The angioplasty guide wire has a length that is substantially longer than the angioplasty, stent or laser catheters.

Furthermore, in many instances, multiple different angioplasty catheters may be used during an operation. In such cases, one catheter is removed by sliding it out of the artery of the patient over the angioplasty guide wire while the angioplasty guide wire remains in place, which is at the desired location in the patient. Another angioplasty catheter is then slid over the angioplasty guide wire and is maneuvered into position, and the operation continues. The angioplasty guide wire must be handled during insertion of the additional angioplasty catheter.

In a conventional operating room situation, the tail end of the angioplasty guide wire sticks out of the femoral artery and gets in the way of surgical personnel and other tubes and devices in the operating field. The angioplasty guide wire is a nuisance and can fall from the operating field and become contaminated. The angioplasty guide wire is also relatively difficult to handle and can become kinked and inoperative if it is not kept in place.

Accordingly, and in order to eliminate the problems associated with handling angioplasty guide wires, and the like, it is an objective of the present invention to provide for a surgical attachment device that is used to secure a small diameter wire or tube, such as an angioplasty guide wire during an operation, along with various catheters used during the operation.

SUMMARY OF THE INVENTION

In order to meet the above and other objectives, the present invention is a surgical attachment device for securing a small diameter wire or tube, and specifically an angioplasty guide wire and angioplasty catheter, stent catheter, or laser catheter used during an angioplasty, stent or laser operation. In one embodiment, the surgical attachment device comprises first and second flexible portions with adjacent abutting surfaces, and a base portion. The abutting surfaces may be flat, or there may be a tapered step formed in one flexible portion and a groove formed in the other flexible portion.

A hole or opening is formed at the interface between the abutting flexible portions. The opening is used to loosely secure the angioplasty guide wire and angioplasty catheter, stent catheter, or laser catheter. The opening is opened by moving the first and second flexible portions toward the base portion which separates the abutting flexible portions to expand the opening.

An adhesive layer is disposed on the bottom of the base portion that is used to secure the surgical attachment device during the operation. The adhesive layer may be affixed or otherwise coated onto the bottom of the member and a backing layer may be disposed thereon. The backing layer covers the adhesive layer prior to use, and is removed to expose the adhesive layer and secure the surgical attachment device to the operating field or drape, for example.

A second embodiment of the surgical attachment device that has been reduced to practice has a unique structure that is optimized for manufacturing using plastic molding processes. The second embodiment of the surgical attachment device has a central tube that is completely closed when it is normally closed, has a diameter the is relatively large compared to the angioplasty guide wire, angioplasty catheter, stent catheter, and laser catheter, or multiple such elements, so that one or more of them may be enclosed by the opening to keep them from moving.

The upper portion of the central tube is cut so that it may be opened, and the wall of the central tube extends upward and outward in both lateral directions away from the tube to form the first and second flexible portions that are depressed to open the central tube. Upper adjacent edges of the central tube abut each other when the central tube and surgical attachment device are in a normally closed position. The first and second flexible portions are tapered or outwardly flared adjacent the opening to form an entry for the opening. The first and second flexible portions have a similar thickness relative to the thickness of the wall of the opening. A transverse rib is formed as part of each of the flexible portions to provide stiffness. The first and second flexible portions have depression formed at their ends distal from the entry to provide a surface that is easy to push on to open the opening.

The opening must be completely closed during use to keep the wire and catheter from being pulled from the device through a gap between the abutting portions, because the wire typically has a diameter on the order of about 0.015 inches, and the catheters typically have a diameter on the order of about 0.15 inches. However, the opening must have the ability to be opened so that ports on the end of the catheters may be moved past the device when the catheters are inserted into the patient.

Instead of having a single base portion, the second embodiment of the surgical attachment device has first and second separate base portions. The first and second base portions are connected to the external wall of the central tube by flanges. A transverse rib is formed as part of each of the base portions to provide stiffness. The first and second base portions are flexible owing to their flange connection to the central tube. An adhesive layer with its backing layer may be disposed on the bottom of the base portion that is used to secure the surgical attachment device during the operation.

The structure of the second embodiment of the surgical attachment device has been optimized for easy manufacture using plastic molding processes. The use of separate base portions allow the opening to close when the device is removed from the mold and allowed to cool, which insures that the device will function properly after manufacture. The structure of a plastic embodiment of the surgical attachment device is relatively flexible and easy to open to pass the angioplasty guide wire and catheter, but is rigid enough to be secured and handled during use. The upper portion of the device is constructed to allow easy opening and closing of the device with one hand by a physician.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
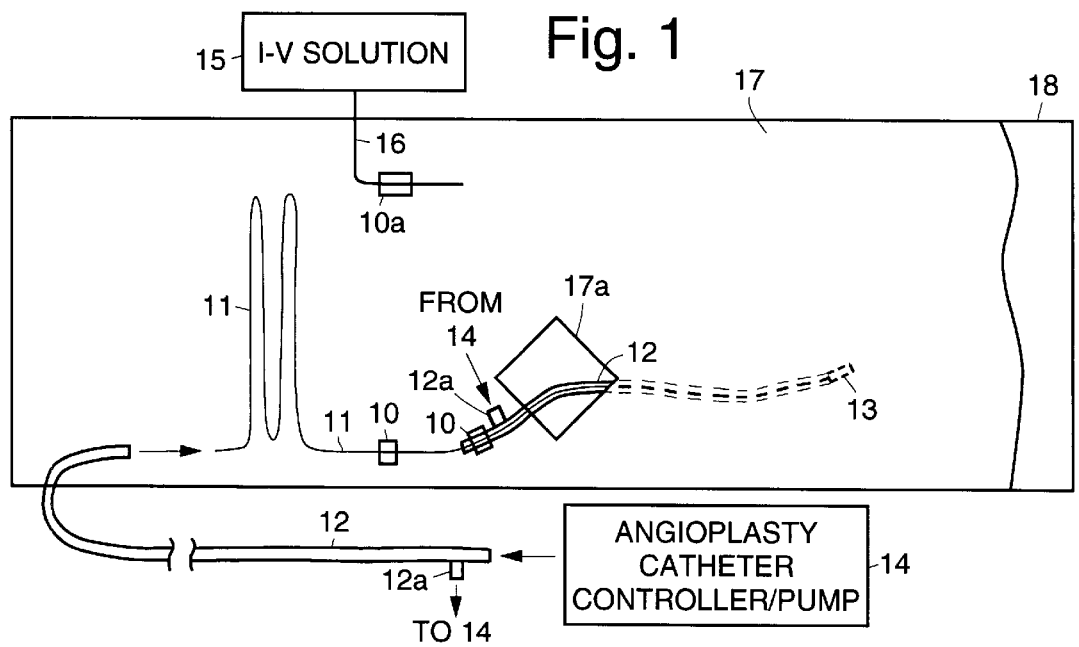
FIG. 1 shows a typical operating room scenario employing a surgical attachment device in accordance with the principles of the present invention.

Referring to the drawing figures, FIG. 1 shows a typical operating room scenario for an angioplasty operation employing surgical attachment devices 10 in accordance with the principles of the present invention, along with surgical attachment devices 10a described with reference to the above-cited patent applications. FIG. 1 shows an operating room table 18 on which is disposed a surgical drape 17 that is used to cover a patient (not shown) during an operation, and in the case of the present invention, an angioplasty operation involving the use of angioplasty guide wires 11 and angioplasty catheters 12. The drape 17 has an opening 17a therein that exposes an area of the patient through which the operation is to be performed. A variety of tubing may employed during the operation, including a flexible intravenous (I-V) line 16 that is run from an I-V solution bag 15 to the patient, for example. With particular relevance to angioplasty operations, the catheter 12 may be coupled to an angioplasty catheter controller and or pump 14 enlarge a balloon 13 and/or stent 13 or to control a laser device 13 during the angioplasty operation.

The surgical attachment devices 10a described in the above-cited patent applications may be used to tightly secure the intravenous (I-V) line 16, or other tubes or cables, in an orderly manner during the operation. The surgical attachment devices 10 of the present invention are used to loosely secure an angioplasty guide wire 11 along with a catheter 12 during an angioplasty operation, in order to keep these elements from becoming contaminated by falling on the operating room floor, while also allowing them to be easily changed during the operation.

Figure 2:
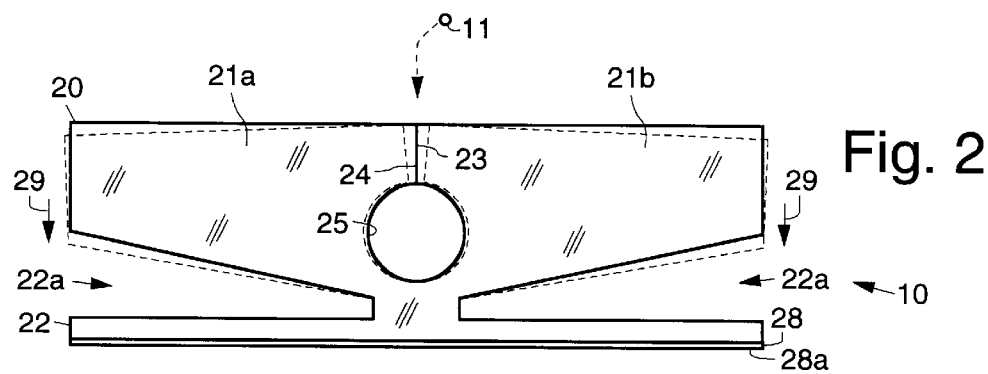
FIG. 2 is an end view of a first embodiment of the surgical attachment device in accordance with the present invention.
Figure 3:
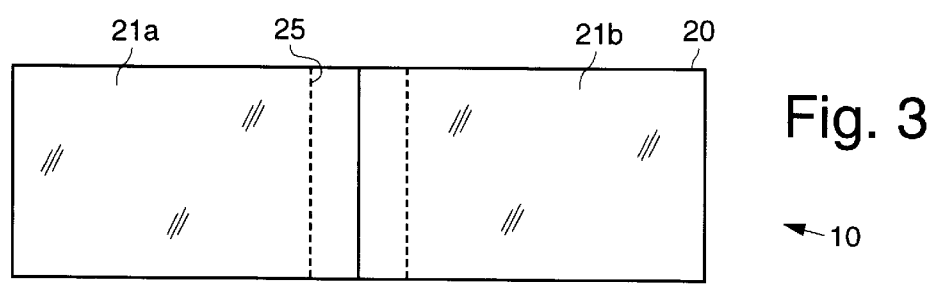
FIG. 3 is a top view of the surgical attachment device of FIG. 2.

Referring now to FIG. 2, it shows an end view of a first embodiment of the surgical attachment device 10 in accordance with the present invention. FIG. 3 is a top view of the surgical attachment device 10 of FIG. 2.

The first embodiment of the surgical attachment device 10 is preferably comprised of molded plastic and includes a flexible member 20 having first and second abutting flexible portions 21a, 21b and a base portion 22. The flexible member 20 may be formed by molding plastic, such as polyproylene, for example. A longitudinal opening 25 through the flexible member 20. The opening 25 that has a diameter that is adapted to loosely secure the angioplasty guide wire 11 and catheter 12.

The flexible member 20 is a single piece structure that has a plurality of inwardly extending wedge-shaped grooves 22a, for example, formed between the first and second flexible portions 21a, 21b and the base portion 22 that extend toward the center of the device 10. The configuration of the first and second flexible portions 21a, 21b, opening 25 and base portion 22 permit the first and second flexible portions 21a, 21b to flex toward the base portion 22, indicated by the phantom lines in FIG. 2 at the periphery of the first and second flexible portions 21a, 21b.

The first and second flexible portions 21a, 21b abut each other when the device 10 is in a normally closed position, so that the opening 25 is fully closed. This is achieved by proper molding techniques and mold tolerances, wherein the molded plastic device 10 cools after molding, and wherein the device 10, and in particular the first and second flexible portions 21a, 21b shrink subsequent to molding to that they abut each other.

It is possible, however, to create the first and second flexible portions 21a, 21b by forming the longitudinal opening 25 through a solid flexible member 20 having 22b, s 22a, 22b, and cutting the top portion thereof between the top of the longitudinal opening 25 and a top surface of the flexible member 20 (distal from the base 22) using a laser, for example, as long as the width of the cut is smaller than the diameter of the guide wire 11.

In the first embodiment of the surgical attachment device 10, abutting surfaces 23, 24 of the cut flexible member 20 are flat above the opening 25. The opening 25 may have a diameter on the order of 0.4 inches. Preferably, the opening 25 should be fully closed during use to keep the wire 11 and catheter 12 from being pulled from the device 10 through a gap between the abutting portions, because the wire 11 typically has a diameter on the order of about 0.15 inches, while the catheters typically have a diameter on the order of about 0.15 inches. However, the opening 25 must have the ability to be opened so that ports 12a on the end of the catheters 12 may be moved past the device 10 when the catheters 12 are inserted into the patient.

The opening 25 is opened to secure the angioplasty guide wire 11 and catheter 12 therein. The opening 25 is opened by moving the first and second flexible portions 21a, 21b toward the base portion 22, which separates them to open the opening 25. Movement of the first and second flexible portions 21a, 21b toward the base portion 22 is indicated by downward pointing arrows 29 in FIG. 2. The angioplasty guide wire 11 and catheter 12 may be inserted into the opening 26 when the first and second flexible portions 21a, 21b are flexed toward the base 22, and is held within the opening 25 when the first and second flexible portions 21a, 21b returned to their unflexed positions.

An adhesive layer 28 is disposed on a bottom surface of the base portion 22 that is used to secure the surgical attachment device 10 during the operation. The adhesive layer 28 may be comprised of any suitable adhesive, such as those commonly used in medical applications. The adhesive layer 28 may be affixed or otherwise coated onto the bottom surface of the flexible member 20 and a backing layer 28a may be disposed thereon. The backing layer 28a is used to cover the adhesive layer 28 prior to use, and is removed to expose the adhesive layer 28, whereafter the surgical attachment device 10 is secured to the drape 17, for example.

Figure 4:
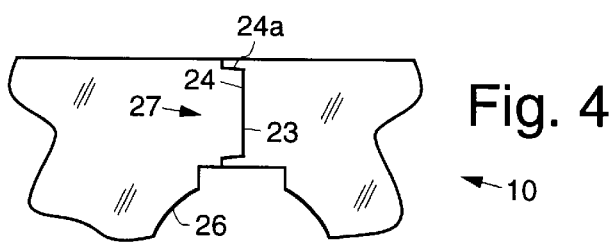
FIG. 4 is an end view of a portion of a second embodiment of the present surgical attachment device.

FIG. 4 shows an end view of a top portion of a second embodiment of the surgical attachment device 10. In the second embodiment of the surgical attachment device 10, the abutting surfaces 23, 24 are comprised of a tapered step 24a formed in one flexible portion 21a and a tapered groove 27 formed in the other flexible portion 21b.

It is to be understood that while the embodiments shown in FIGS. 2–4 illustrate an opening 26 for use with angioplasty guide wire 11, the sizing of the opening may be altered to meet particular requirement for different size wires 11 or catheters 12. Consequently, the embodiments of the surgical attachment device 10 shown in FIGS. 2–4 should not be taken as limiting.

The surgical attachment device 10 may have a length of about 1.50 inches, a width of about 2.00 inches, and a thickness of about 1.00 inches, for example. With respect to the opening 26 shown in FIG. 2, it may have a diameter of from 0.4 inches, for example.

Figure 5:
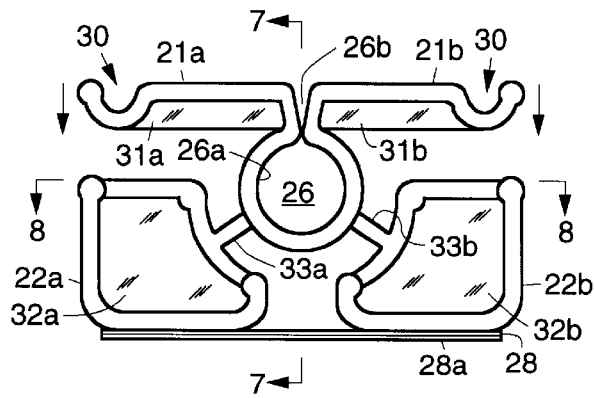
FIG. 5 is an end view of third embodiment of the present surgical attachment device which has been reduced to practice.
Figure 6:
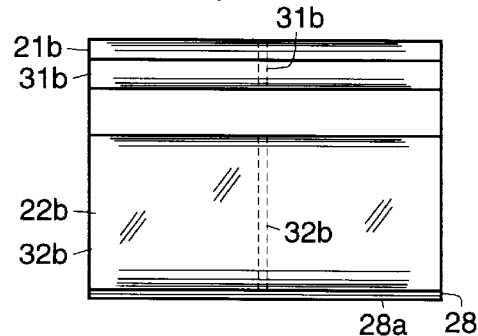
FIG. 6 shows a side view of the surgical attachment device of FIG. 5.
Figure 7:
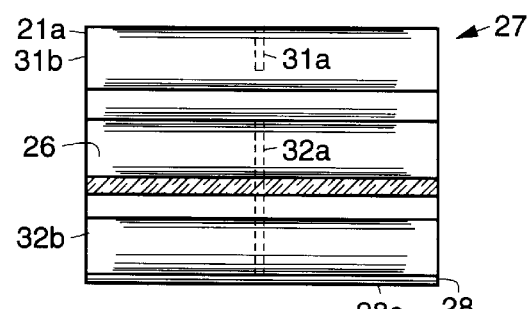
FIG. 7 is a cross sectional side view of the device of FIG. 5 taken along the lines 7—7.
Figure 8:
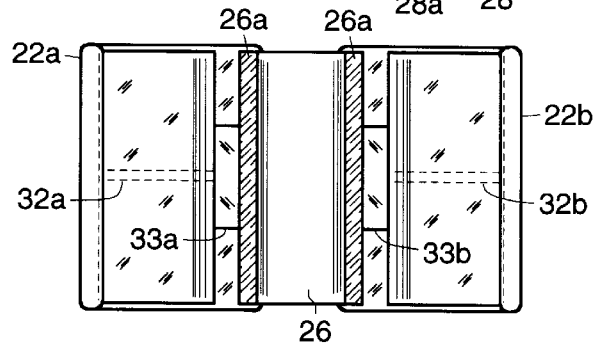
FIG. 8 is a cross sectional top view of the device of FIG. 5 taken along the lines 8—8.

Referring to FIG. 5, it shows an end view of third and preferred embodiment of the present surgical attachment device 10. FIG. 6 shows a side view of the surgical attachment device of FIG. 5, FIG. 7 is a cross sectional side view of the device of FIG. 5 taken along the lines 7—7, and FIG. 8 is a cross sectional top view of the device of FIG. 5 taken along the lines 8—8.

The second embodiment of the surgical attachment device 10 has a unique structure that is optimized for manufacturing using plastic molding processes. The second embodiment of the surgical attachment device 10 has a central tube 26 or opening 26 that has a diameter designed to loosely secure the angioplasty guide wire 11 and catheter 12 (FIG. 1).

The uppermost portion of the opening 26 is made so that it may be opened or spread apart, and a wall 26a of the opening 26 extends upward and outward in both lateral directions away from the opening 26 to form the first and second flexible portions 21a, 21b that are depressed to open the opening 26. At least a portion of the upper adjacent edges of the opening 26 abut each other when the opening 26 and surgical attachment device 10 are in a normally closed position. The first and second flexible portions 21a, 21b may be tapered or outwardly flared adjacent the opening 26 to form an entry 26b for the opening 26. The first and second flexible portions 21a, 21b are about the same thickness as the wall 26a of the opening 26. The first and second flexible portions 21a, 21b are rounded at their edges. The first and second flexible portions 21a, 21b have depressions 30 formed at ends distal from the entry 26b to provide a surface that is easy depressed to open the opening 26. The first and second flexible portions 21a, 21b have transverse ribs 31a, 31b formed beneath their respective top surfaces to provide added strength.

Instead of having a single base portion 22, the second embodiment of the surgical attachment device 10 has first and second separate base portions 22a, 22b. The first and second base portions 22a, 22b are connected to the external wall 26a of the opening 26 by flanges 33a, 33b. The first and second base portions 22a, 22b are rounded at their edges. The first and second base portions 22a, 22b have transverse ribs 32a, 32b formed between their respective flange 31, 33b and the peripheries thereof to provide added strength. The first and second base portions 22a, 22b are flexible owing to their flange connection to the opening 26. An adhesive layer 28 with its backing layer 28a may be disposed on the bottom of the base portions 22a, 22b that is used to secure the surgical attachment device 10 during the operation.

The structure of the second embodiment of the surgical attachment device 10 has been optimized for easy manufacture using plastic molding processes. The structure of a plastic embodiment of the surgical attachment device 10 is relatively flexible and easy to open to insert angioplasty guide wires 11 and catheters 12, for example, but is rigid enough to be secured and handled during use.

Figure 9A:
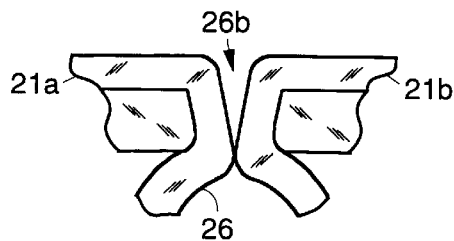
FIGS. 9a and 9b are enlarged views that illustrate closed and opened positions of the surgical attachment device of FIG. 5.
Figure 9B:
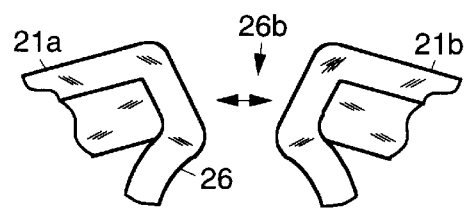

FIGS. 9a and 9b are enlarged views that illustrate closed and opened positions of the surgical attachment device 10 of FIG. 5. In FIG. 9a, which illustrates the closed position, the adjacent portions of the wall 26a of the opening 26 abut each other so that the opening 26 is closed. In FIG. 9b, illustrating the open position, the first and second flexible portions 21a, 21b have been moved toward the respective base portions 22a, 22b (indicated by the downward pointing arrows adjacent the flexible portions 21a, 21b in FIG. 5) which causes the adjacent portions of the wall 26a of the opening 26 to move apart, thus providing an entry to the opening 26 so that the angioplasty guide wire 11 and catheter 12 may be inserted therein.

The surgical attachment devices 10 are preferably manufactured by molding as a single piece device. The adhesive layer 28 may then coated or disposed on the base portions 22a, 22b and the backing layer 28a applied to the exposed surface of the adhesive layer 28. Alternatively, the adhesive layer 28 and the backing layer 28a may be fabricated as a decal which is applied to the bottom surface or surfaces of the base portion 22 or portions 22a, 22b. This assembly is then packaged, and the packaged assembly is sterilized by means of gamma radiation sterilization procedures commonly used in the medical industry.

During an operation, one or more sterilized packages are opened, and the surgical attachment devices 10 are removed from the packages. By way of example, the backing layer 28a may be removed from each surgical attachment device 10 to expose the adhesive layer 28, and each device 10 may be secured to the surgical drape 17, for example, in an appropriate place relative to the location of the patient and angioplasty guide wire 11 and catheter 12 that are to be secured.

Although several options are available, the catheter 12 may be threaded over the guide wire 11 and the first and second flexible portions 21a, 21b of the device 10 closest to the patient may be depressed so that the angioplasty guide wire 11 and catheter 12 placed in the opening 26. The guide wire 11 and catheter 12 are then inserted into the patient to the proper location. The guide wire 11 is substantially longer than the catheter 12 and the catheter 12 has a port 12a at its rear end that is used to inflate the balloon and inject dye into the artery of the patient. When the port 12a of the catheter 12 reaches the device, the first and second flexible portions 21a, 21b of the device 10 may again be depressed to move the port 12a past the device 10, if desired.

In any event, the angioplasty guide wire 11 and (and possibly the catheter 12) are confined by the device 10. The device 10 thus prevents the guide wire 11 from becoming contaminated, and also prevents the guide wire 11 and catheter 12 from interfering with the operation.

In the event that multiple angioplasty catheters are required during an operation, the used catheter 12 is removed from the patient, keeping the guide wire 11 in place. The catheter 12 is slid using the angioplasty guide wire 11 as a guide, and which involves expanding the opening 26 and removing the used catheter 12 from the surgical attachment device 10, and then sliding the used catheter 12 off of the exposed end of the guide wire 11. A different catheter 12 is then inserted using the angioplasty guide wire 11 as a guide. The opening of each device 10 that is employed is opened when required to pass the port 12a past it. The catheter 12 is again maneuvered to the appropriate location within the patient using the guide wire 11, while the guide wire 11 remains secured in the appropriate surgical attachment devices 10.

Thus new and improved surgical attachment devices that may be used to loosely secure a small diameter wire or tube, such as an angioplasty guide wire during an operation, along with various catheters used during the operation. It is to be understood that the above-described embodiments are merely illustrative of some of the many specific embodiments which represent applications of the principles of the present invention. Clearly, numerous and other arrangements can be readily devised by those skilled in the art without departing from the scope of the invention.

What is claimed is:

1. Apparatus comprising:
   a flexible member comprising:
      a base portion;
      first and second abutting flexible portions attached to the base portion that are separated from the base portion by grooves that permit the first and second flexible portions to flex toward the base portion;
      a longitudinal opening formed at an interface between the abutting flexible portions; and
      an adhesive layer disposed on a bottom surface of the flexible member.

2. The apparatus of claim 1 wherein abutting surfaces of the first and second abutting flexible portions are flat.

3. The apparatus of claim 1 wherein abutting surfaces are comprised of a tapered step formed in one flexible portion and a tapered groove formed in the other flexible portion.

4. The apparatus of claim 1 wherein the opening is dimensioned to loosely secure an angioplasty guide wire and catheter therein.

5. The apparatus of claim 1 wherein the opening has a diameter on the order of 0.4 inches.

6. The apparatus of claim 1 wherein the adhesive layer has a backing layer disposed thereon.

7. The apparatus of claim 1 wherein the base portion comprises first and second base portions.

8. Apparatus comprising:
   a flexible member having an opening therethrough, which member is cut at its top to form an entry to the opening that forms upper adjacent edges that abut each other when the apparatus is in a normally closed position;
   first and second flexible portions extending outward in lateral directions away from the entry to the opening that are depressible to separate the upper adjacent edges and open the entry to the opening;
   first and second base portions connected to the member; and
   an adhesive layer disposed on bottom surfaces of the base portions.

9. The apparatus of claim 8 wherein the first and second flexible portions are connected to the member by flanges to form flanged connections and are flexible due to their flanged connections to the member.

10. The apparatus of claim 8 wherein the first and second flexible portions have proximal ends which are tapered adjacent their proximal ends to form an entry to the opening.

11. The apparatus of claim 8 wherein the opening has a diameter designed to loosely secure an angioplasty guide wire and catheter.

12. The apparatus of claim 8 wherein the first and second flexible portions each have a rib extending from the top of the opening to a distal end of the respective flexible portion, and wherein the first and second base portions each have a transverse rib formed between their respective flange and a periphery of the respective base portion.

* * * * *